US012285721B1

(12) United States Patent
McDaniel (10) Patent No.: US 12,285,721 B1
(45) Date of Patent: Apr. 29, 2025

(54) DEVICES, METHODS, AND SYSTEMS FOR CAPTURING AND SEQUESTERING ATMOSPHERIC GASES

(71) Applicant: Like Lichen LLC, Austin, TX (US)

(72) Inventor: Claude Steven McDaniel, Austin, TX (US)

(73) Assignee: LIKE LICHEN LLC, Austin, TX (US)

( * ) Notice: Subject to any disclaimer, the term of this patent is extended or adjusted under 35 U.S.C. 154(b) by 0 days.

(21) Appl. No.: 18/484,702

(22) Filed: Oct. 11, 2023

(51) Int. Cl.
*B01D 53/84* (2006.01)
*B01D 53/62* (2006.01)
*C12N 1/12* (2006.01)

(52) U.S. Cl.
CPC .............. *B01D 53/84* (2013.01); *B01D 53/62* (2013.01); *C12N 1/12* (2013.01); *B01D 2251/95* (2013.01); *B01D 2257/504* (2013.01); *B01D 2258/06* (2013.01)

(58) Field of Classification Search
CPC .... B01D 53/84; B01D 53/62; B01D 2251/95; B01D 2257/504; B01D 2258/06; C12N 1/12
USPC ......................................................... 435/266
See application file for complete search history.

(56) References Cited

U.S. PATENT DOCUMENTS

| 7,132,247 | B1 | 11/2006 | Lyngberg et al. |
| 7,745,023 | B2 | 6/2010 | Flickinger et al. |
| 7,998,714 | B2 * | 8/2011 | Gellett ............... B01D 53/75 |
| | | | 435/174 |
| 8,361,768 | B2 | 1/2013 | Wang et al. |
| 8,715,393 | B2 | 5/2014 | Wright et al. |
| 9,457,340 | B2 | 10/2016 | Buelow et al. |
| 9,714,406 | B2 * | 7/2017 | Constantz ............. B01D 53/62 |
| 9,790,484 | B2 | 10/2017 | Wackett et al. |
| 10,035,719 | B2 | 7/2018 | Novak et al. |
| 2005/0260553 | A1 | 11/2005 | Berzin |
| 2008/0085536 | A1 | 4/2008 | Nobles et al. |
| 2008/0113413 | A1 | 5/2008 | Nobles et al. |
| 2008/0124767 | A1 | 5/2008 | Nobles et al. |
| 2009/0126265 | A1 * | 5/2009 | Rasmussen ............ C12M 41/34 |
| | | | 47/1.4 |

(Continued)

FOREIGN PATENT DOCUMENTS

| ES | 2420519 B1 * | 10/2014 | ............ F26B 17/003 |
| JP | H0957058 | 3/1997 | |

(Continued)

OTHER PUBLICATIONS

ES2420519B1 Machine English Translation (Year: 2014).*

(Continued)

*Primary Examiner* — Michael L Hobbs
*Assistant Examiner* — Lenora A Abel
(74) *Attorney, Agent, or Firm* — Kilpatrick Townsend & Stockton LLP (57) ABSTRACT

A carbon dioxide capture and sequestration system comprises a growth module, a drying module, a sequestration module and a carbon dioxide recapture apparatus. The carbon dioxide recapture apparatus includes at least one conduit coupled to the growth module, the drying module, and the sequestration module for routing carbon dioxide liberated from at least one of the harvested algal biomass within the drying module and the dried algal biomass within the sequestration module to the growth module.

20 Claims, 5 Drawing Sheets

(56) References Cited

U.S. PATENT DOCUMENTS

| | | | |
|---|---|---|---|
| 2009/0181434 A1 | 7/2009 | Aikens et al. | |
| 2010/0124583 A1* | 5/2010 | Medoff | C12P 13/14 |
| | | | 536/56 |
| 2011/0003345 A1 | 1/2011 | Nobles et al. | |
| 2011/0016773 A1 | 1/2011 | Nichols et al. | |
| 2012/0100603 A1 | 4/2012 | Lewnard et al. | |
| 2013/0224826 A1 | 8/2013 | Wang et al. | |
| 2014/0127776 A1* | 5/2014 | Picard | C12M 23/48 |
| | | | 435/178 |
| 2014/0242676 A1 | 8/2014 | Abdel-Fattah et al. | |
| 2016/0175634 A1 | 1/2016 | Radian et al. | |
| 2016/0194599 A1 | 7/2016 | Kanehara | |
| 2021/0093998 A1 | 4/2021 | Küpper | |
| 2021/0260527 A1 | 8/2021 | McDaniel | |
| 2022/0387928 A1 | 12/2022 | Chang et al. | |

FOREIGN PATENT DOCUMENTS

| | | |
|---|---|---|
| WO | 2011036517 A1 | 3/2011 |
| WO | 2014113740 A1 | 7/2014 |

OTHER PUBLICATIONS

Choudhary, Post Storage Potential of Nostoc linckia (Cyanobacteria) immobilized in CA Alginate (synthetic seed) as biofertilizer inocula, Journal of General Applied Microbiology, May 5, 2011, pp. 247-251, vol. 57.

Bernal, Specific Photosynthetic Rate Enhancement by Cyanobacteria Coated Onto Paper Enables Engineering of Highly Reactive Cellular Biocomposite "Leaves", Biotechnology and Bioengineering, Oct. 2014, pp. 993-2008, vol. 111, No. 10, Wiley Periodicals Inc.

Eckardt et al., Growth and Photosynthesis under High and Low Irradiance of Arabidopsis thaliana Antisense Mutants with Reduced Ri bulose-I,5 -B isphosphate Carboxylase/Oxygenase Activase Content, Plant Physiology, 1997, pp. 575-586, vol. 113, American Society of Plant Biologists.

Bernal et al., Fabrication of Photoreactive Biocomposite Coatings via Electric Field-Assisted Assembly of Cyanobacteria, Langmuir, May 8, 2017, 5304-5313, vol. 33, American Chemical Society.

Bernal et al., Microbial Paper: Cellulose Fiber-based Photo-Absorber Producing Hydrogen Gas from Acetate Using Dry Stabilized Rhodopsuedomonas palustris, Bioresource.com, Apr. 18, 2017, 4013-4030.

Zhao et al., High-yield production of extracellular type-I cellulose by the cyanobacterium Synechococcus sp. PCC 7002, Cell Discovery, Apr. 28, 2018, pp. 1-12.

Cortez et al., Biocoatings: A new challenge for environmental biotechnology, Biochemical Engineering Journal, Jan. 19, 2017, pp. 25-37, Elsevier B.V.

Lode et al., Green bioprinting: Fabrication of photosynthetic algae-laden hydrogel scaffolds for biotechnological and medical applications, Engineering in Life Sciences, Jan. 7, 2015, pp. 1-7, 2015 WILEY-VCH Verlag GmbH & Co.

Flickinger et al., Painting and Printing Living Bacteria: Engineering Nanoporous Biocatalytic Coatings to Preserve Microbial Viability and Intensify Reactivity, Biotechnol. Prog., Jan. 5, 2007, vol. 23, No. 1, pp. 2-17, American Chemical Society and American Institute of Chemical Engineers.

Haoyang, Algae-Based Carbon Sequestration, IOP Conf. Series: Earth and Environmental Science, 2018, pp. 1-9, IOP Publishing.

Nobles et al., Cellulose in Cyanobacteria. Origin of Vascular Plant Cellulose Synthase?, Plant Physiology, Oct. 2001, vol. 127, pp. 529-542, American Society of Plant Biologists.

Stinson, "Leaf-shaped wall tiles use algae to purify wastewater", Apr. 4, 2019 (Apr. 4, 2019), retrieved on Jun. 23, 2020 from https://www.curbed.com/2019/4/4/18294595/algae-wall-tiles-purify-wastewater-industry.

Allaboutalgae, "Algae Basics", Nov. 9, 2018 (Nov. 9, 2018), retrieved on Jun. 24, 2020 from https://web.archive.org/web/20181109064911/http://allaboutalgae.com/benefits/.

Larraneta, "Water-retaining hydrogels—the unsung heroes of medicine", Oct. 21, 2016 (Oct. 21, 2016), retrieved on Jun. 23, 2020 from https://theconversation.com/water-retaining-hydrogels-the-unsung-heroes-of-medicine-66149.

International Search Report and Written Opinion, dated Jul. 14, 2020, PCT/US20/28404.

Gosse et al., "Hydrogen Production by Photoreactive Nanoporous Latex Coatings of Nongrowing Rhodopseudomonas palustris CGA009", American Chemical Society and American Institute of Chemical Engineers, Biotechnol. Prog., 2007, vol. 23, No. 1, published Dec. 23, 2006, pp. 124-130.

PCT/US2024/050434, "International Search Report and Written Opinion", Dec. 18, 2024, 13 pages.

* cited by examiner

DEVICES, METHODS, AND SYSTEMS FOR CAPTURING AND SEQUESTERING ATMOSPHERIC GASES

FIELD OF THE DISCLOSURE

The disclosures made herein relate generally to chemical processing and, more particularly, to devices, methods, and systems for capturing and sequestering atmospheric gases. Even more particularly, the disclosures made herein relate to devices, methods, and systems for capturing carbon dioxide ($CO_2$) from a gaseous environment such as, for example, the earth's atmosphere to enable long-term storage, utilization or atmospheric balancing of such captured carbon dioxide (i.e., carbon dioxide sequestration, captured carbon utilization and/or the like).

BACKGROUND

Figure 1:
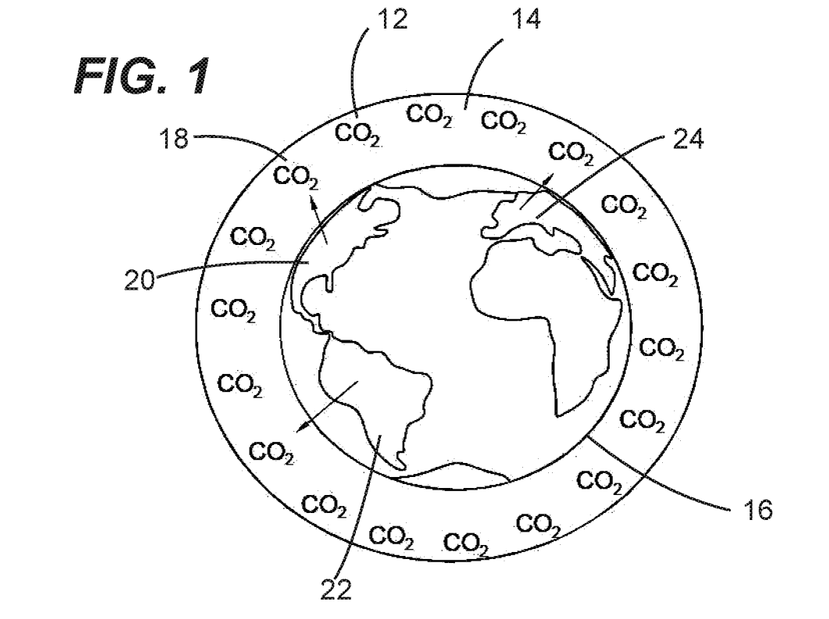
FIG. 1 is an illustrative view showing a representation of carbon dioxide in Earth's atmosphere, with release of additional carbon dioxide due to man-made activities.

It is well known that carbon dioxide is a by-product of both naturally-occurring activities and man-made activities. Examples of such naturally-occurring activities include, but are not limited to, animal respiration, decomposition of formerly living organisms, weathering of carbonate rocks, volcanic eruptions, plant (e.g., forest) fires and the like. Examples of such man-made activities include, but are not limited to, fossil fuel use, intentional burning of biomass (e.g., wood stoves, intentional or unintentional forest fires), cement production, ammonia production and the like. However, as shown in FIG. 1, the current increase in carbon dioxide 12 in Earth's atmosphere ("air") 14 surrounding the Earth 16 (i.e., atmospheric carbon dioxide 12) is being driven by release of additional carbon dioxide 18 by mostly terrestrial, man-made activities, particularly in industrialized regions such, for example, as North America 20, South American 22, and Western Europe 24.

Figure 2:
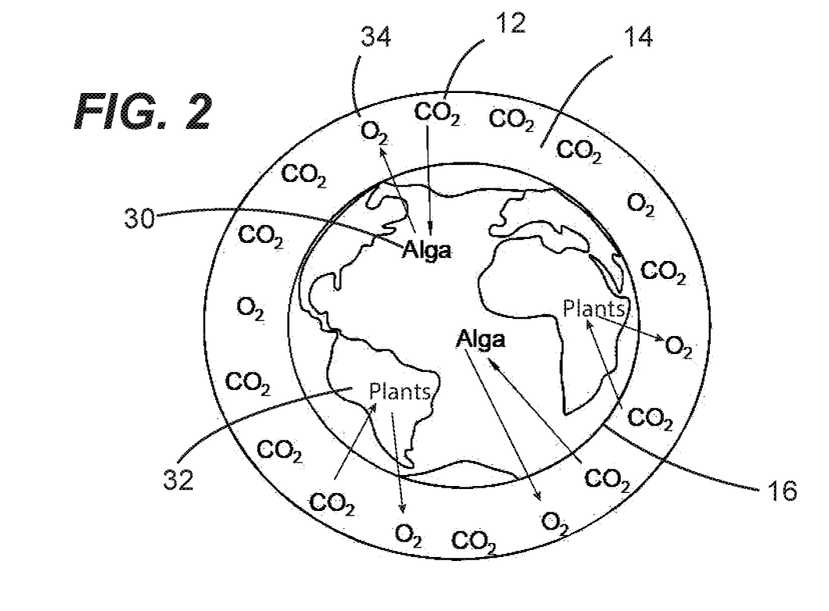
FIG. 2 is an illustrative view showing a representation of ocean-based alga and land-based plant performing photosynthetic conversion of atmospheric carbon dioxide into oxygen that is released into Earth's atmosphere.

Photosynthesis from land-based plants and from ocean-bound algae (i.e., a photosynthetic microorganism) are the two primary naturally-occurring processes for removing carbon dioxide from Earth's atmosphere (i.e., ambient air surrounding the earth). This naturally-occurring photosynthetic conversion of carbon dioxide requires water (e.g., ambient environmental moisture) and sunlight to convert available carbon dioxide in the air to oxygen ($O_2$) and carbohydrates (e.g., saccharides). Of these two naturally occurring sources of photosynthesis, as illustrated in FIG. 2, ocean-bound algae 30 and terrestrial plants 32 (e.g., trees within forests) provide the majority of the photosynthetic capture ("uptake") of atmospheric carbon dioxide 12 from the air 14 surrounding the Earth 16 that results in release of oxygen 34 into the air 14. More specifically, the ocean-bound algae 30 is in the form of a thin layer floating at/near the surface of ocean water. The vast size of the earth's oceans provides a substantial surface area by which these ocean-bound algae 30 can perform the majority (e.g., about 70%) of photosynthetic capture of atmospheric carbon dioxide 12 and release of oxygen 34 into surrounding air 14.

However, as a result of the sheer magnitude of carbon-dioxide resulting from man-made activities, naturally-occurring photosynthetic conversion of carbon dioxide has for many decades been unable to mitigate the amount of carbon-dioxide produced by man-made activities that is being delivered into the earth's atmosphere. As a result, excess amounts of carbon dioxide have built up in the earth's ambient air. For example, it is estimated that the amount of carbon dioxide in the Earth's ambient air has increased from 280 parts per million ("ppm") in the 1700 s to 411 ppm in March 2019 [Eggleton, T. (2012) "A Short Introduction to Climate Change," Cambridge University Press, p. 53; "Up-to-date weekly average $CO_2$ at Mauna Loa" Earth System Research Laboratory Global Monitoring Division, Mauna Loa, Hawaii, Retrieved 03.28.19]. Additionally, to make matters worse, approximately 50 gigatons of additional carbon dioxide equivalents (e.g., greenhouse gases such as carbon dioxide, methane, nitrous oxide, hydrofluorocarbons, perfluorocarbons, sulfur hexafluoride) are released into the Earth's ambient air per year primarily from fossil fuel usage (Bridging the Emissions Gap: A UNEP Synthesis Report, Nairobi, Kenya: United Nations Environment Programme (UNEP), November 2011).

It is also well known that carbon dioxide represents about 80% of greenhouse gas, with methane, nitrous oxide and floriated gases representing the balance. It is also well known that these greenhouse gases are the contributing factor to global warming and the associated climate-change around the globe (e.g., severe storms, warming of the oceans, melting of glaciers, rising sea levels and the like). The current level of greenhouse gases and their projected rate of increase have led experts in the field of climatology to the conclusion that, if left unchecked, further increases in greenhouse gases will result in irreversible climatic changes and resulting catastrophic effects of climate change on people, property and nature.

Therefore, devices, methods, and systems for capturing and sequestering atmospheric carbon dioxide are beneficial, desirable and useful.

SUMMARY OF THE DISCLOSURE

Embodiments of the disclosures made herein are directed to devices, methods, and systems for capturing and sequestering atmospheric carbon dioxide. More particularly, embodiments of the disclosures made herein are directed to devices, methods, and systems for capturing carbon dioxide from a gaseous environment such as for example, the earth's atmosphere, to enable long-term storage, utilization or atmospheric balancing of such carbon dioxide. Excess atmospheric carbon dioxide over and above natural concentrations in the atmosphere is a key contributor to climate change and global warming. It is well known that, in addition to controlling emissions, carbon dioxide must be removed on a permanent basis from the atmosphere. Devices, methods, and systems in accordance with embodiments of the disclosures made herein are configured to aid in addressing this challenge by enabling the conversion of atmospheric carbon dioxide into biomass, which is subsequently sequestered in a manner that provides for negligible re-emission of $CO_2$ from the biomass. Systems in accordance with embodiments of the disclosures made herein are configured for providing long-term sequestration of the carbon dioxide within the biomass. Accordingly, devices, methods, and systems in accordance with embodiments of the disclosures made herein offer beneficial, desirable and useful functionalities.

In one or more embodiments of the disclosures made herein, a carbon dioxide capture and sequestration system comprises a growth module, a drying module, a sequestration module and a carbon dioxide recapture apparatus. The carbon dioxide recapture apparatus includes one or more conduits coupled to the growth module, the drying module, and the sequestration module for routing carbon dioxide liberated from at least one of the harvested algal biomass within the drying module and the dried algal biomass within the sequestration module to the growth module.

In one or more embodiments of the disclosures made herein, a method for performing direct air capture of carbon dioxide comprises a plurality of operations. An operation is performed for growing algal biomass within a first system module. An operation is performed for drying a harvested portion of the algal biomass within in a second system module to produce dried algal biomass. An operation is performed for storing the dried algal biomass within a third system module. An operation is performed for routing carbon dioxide liberated from the algal biomass within at least one of the second system module and the third system module to the first system module for enabling algal biomass to be grown within the first system module using the carbon dioxide liberated from the algal biomass within at least one of the second system module and the third system module.

In some embodiments, a monitoring device is integral with one or more of the growth module, drying module and the sequestration module for enabling a respective level of carbon dioxide therein to be monitored.

In some embodiments, a pump and/or a valve is operably connected to at least one of the drying module and one of the conduits attached to the drying module.

In some embodiments, the drying module includes a moisture content monitoring device operable for monitoring a level of moisture therein.

In some embodiments, the moisture content monitoring device is operably coupled to a pump and/or a valve for enabling operation of the pump and/or the valve as a function of the level of moisture content in the drying module.

In some embodiments, the drying module include a light transmissive top cover that rejects at least 70% of UV rays of sunlight impinging thereon.

In some embodiments, the drying module includes a housing comprising a fluid containment body, a structural frame, a substrate support body, and a light transmissive top cover.

In some embodiments, the fluid containment body has an opening within a top surface thereof.

In some embodiments, the substrate support body includes a substrate support portion within the containment body below the opening therein.

In some embodiments, the light transmissive top cover extends over the opening within a top surface of the containment body.

In some embodiments, the substrate support portion is a first portion of the substrate support body and the substrate support body includes a second portion engaged with a top surface of the fluid containment body for engaging the substrate support body with the fluid containment body.

These and other objects, embodiments, advantages and/or distinctions of the present invention will become readily apparent upon further review of the following specification, associated drawings and appended claims.

DETAILED DESCRIPTION

Figure 3:
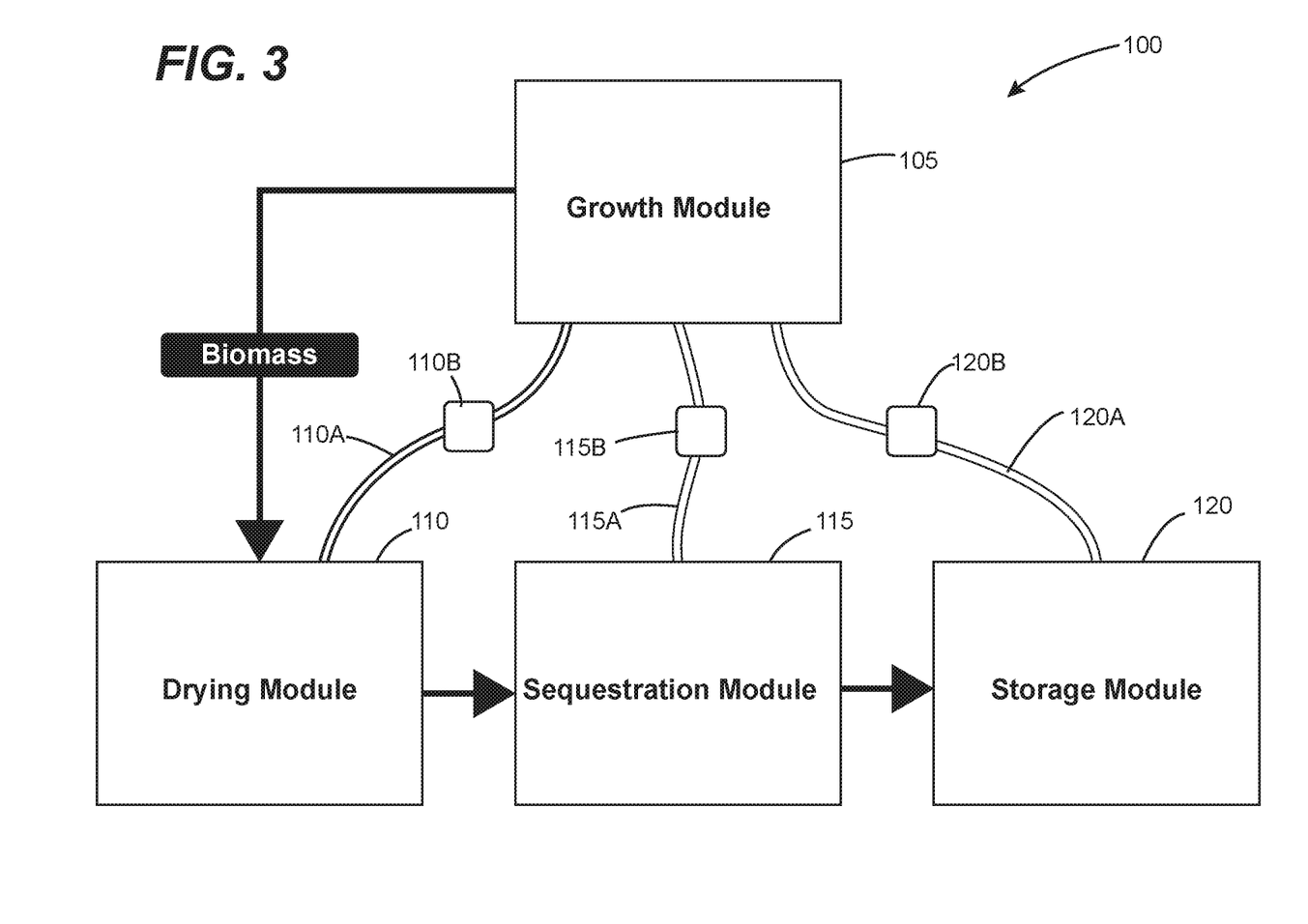
FIG. 3 is diagrammatic view showing a system in accordance with one or more embodiments of the disclosures made herein.

Referring now to FIG. 3, a system in accordance with embodiments of the disclosures made herein (e.g., system 100) and associated methods of operability are discussed. Beneficially, the system 100 and associated method of operability are implemented in a manner that provides for long-term sequestration of the biomass. Such sequestration of the biomass refers to the biomass exhibiting little to no re-emission of carbon dioxide therefrom over an extended period of time—e.g., years, decades, or centuries. For example, in some embodiments, the biomass may be maintained in a dried form within a controlled environment that inhibits or significantly limits re-emission of carbon dioxide from the biomass. In some embodiments, the biomass may be entrapped within a polymeric material within which it was grown.

The system 100 may include a growth module 105 (or a plurality of growth modules), a drying module 110 (or a plurality of drying modules), a sequestration module 115 (or a plurality of sequestration modules), and a storage module 120 (or a plurality of storage modules). The growth module 105 has a construction and associated operability that provides for growth of biomass from atmospheric carbon dioxide (i.e., a carbon-containing biomass derived from atmospheric carbon dioxide). The biomass is grown in a manner that results in the algal biomass having a given amount of moisture content that, if not reduced via drying, would promote considerable amounts of carbon dioxide being liberated (off-gassed) from the biomass over time. The drying module 110 has a construction and associated operability that provides for drying of the biomass grown in the growth module 105 (i.e., dried biomass). Preferably, drying of the biomass is performed in a manner that contributes to inhibiting or significantly limiting both carbon dioxide from being liberated from the biomass over time and re-emission of liberated carbon dioxide back into the atmosphere during its drying. The sequestration module 115 has a construction and associated operability that provides for storage of a first volume of the dried biomass under conditions that inhibit or significantly limit re-emission of carbon dioxide from the dried biomass. The storage module 120 has a construction and associated operability that provides for storage of a second volume of the dried biomass (e.g., greater than the first volume) under conditions inhibit or significantly limit re-emission of carbon dioxide from the dried biomass. Accordingly, the system 100 may provide for the following functionalities: 1.) capturing carbon dioxide directly from air (i.e., direct air capture-DAC) by performing a chemical reaction that converts carbon dioxide in the air to a carbon-containing biomass, 2.) for drying the biomass, and 3.) for storing the biomass under conditions that achieve long-term sequestration of the carbon dioxide of the dried biomass.

Beneficially, the drying module 110, the sequestration module 115, and the storage module 120 may each be coupled to the growth module 105 for enabling re-emitted carbon dioxide to be captured and utilized for algal biomass growth within the growth module 105. For example, in preferred embodiments, an interior enclosed space of each of the drying module 110, the sequestration module 115, and the storage module 120 may be coupled to an interior enclosed space of the growth module 105 through a respective one of a plurality of gas flow conduits 110A, 115A, 120A. It is disclosed herein that only the growth module 105 connected to the gas flow conduits 110A, 115A, 120A may have a sealed interior space whereby other growth modules (not shown) of the system 100 have an interior space that is exposed to a surrounding atmospheric environment or other type of surrounding environment. It is also disclosed herein that all growth modules 105 of the system 100 may have a sealed interior space.

In some embodiments, the gas flow conduits 110A, 115A, 120A (e.g., pipes, tubing, ductwork, or the like) may be coupled to the growth module 105 through a manifold structure (e.g., a 3-into-one collector structure) that provides for gas flow from the gas flow conduits 110A, 115A, 120A merge into gas flow through a single gas flow conduit. Each of the gas flow conduits 110A, 115A, 120A and/or the manifold structure may include one or more flow control devices 110B, 115B, 120B (e.g., pumping device(s), one-way flow device(s), on-off valve(s), monitoring device(s) for operating parameters, etc.) that induce and/or inhibit and/or monitor the flow of gas from a respective one of the drying, sequestration, and storage modules 110, 115, 120 to the growth module 105. The one or more flow control devices 110B, 115B, 120B may also be integral with one or both of the module at opposing ends of a respective one of the conduits 110A, 115A, 120A. For example, the growing module 105 and/or the drying module 110 may include one or more flow control devices 110B integral therewith. In these regards, it is disclosed herein the system 100 may include one or more feedback circuits provide for re-capture and sequestration of at least a portion of carbon dioxide that is liberated (i.e., emitted) from biomass contained within one or more of the drying module 110, the sequestration 115, and the storage module 120. Accordingly, methods, and systems in accordance with embodiments of the disclosures made herein preferably may include one or more feedback circuits provide for re-capture and sequestration of at least a portion of carbon dioxide that is liberated from biomass that is being dried and/or stored.

The aforementioned one or more feedback circuits provide for an artificial carbon cycle during the duration of operation of the system 100. The one or more feedback circuits enable the system 100 to operate in a fully closed-loop mode of operation or a substantially closed-loop mode of operation. Specifically, in a first part of the loop (i.e., in a first part of the system), a portion of carbon dioxide liberated from biomass (e.g., algal biomass) sequestered in a second part of the loop (i.e., in a second part of the system) is captured and, in the second part of the loop, biomass produced using the liberated carbon dioxide in the first part of the loop is sequestered. Here, the first part of the loop may be the growth module 105 and the second part of the loop may be a combination of the drying module 110 and the sequestration module 115 (and optionally the storage module 120). Through implementation of this artificial carbon cycle, the system 100 and embodiments of other systems in accordance with the disclosures made herein are able to capture all or at least a significant portion of carbon dioxide liberated from biomass within the operational boundary of the system and then use that captured liberated carbon dioxide to produce biomass within the operational boundary of the system.

In some embodiments, a monitoring device is mounted within (e.g., integral with) the drying module and/or the sequestration module for enabling a respective level of carbon dioxide therein to be monitored and a pump and/or a valve is operably connected to at least one of the one or more of the conduits, the growth module, the drying module, and the sequestration module for controlling flow of the liberated carbon dioxide flowing therein. The pump and/or the valve is coupled to the monitoring device and is adapted to operate as a function of the respective level of carbon dioxide within the associated one of the one or more conduits, the growth module, the drying module, and the sequestration module.

The growth module 105 (e.g., a first system module) may utilize known or yet to be conceived techniques for implementing growth of carbon-containing biomass utilizing atmospheric carbon dioxide as a source of carbon. Some preferred biological techniques for implementing growth of carbon-containing biomass utilize the photosynthetic characteristic of algae for converting atmospheric carbon dioxide to biomass. As is well known, algae subjected to sunlight, water, and atmospheric carbon dioxide results in photosynthetic activity that produces new molecules of algae—i.e., algal biomass growth from an initial starting amount of algal biomass. At a given timeframe during algal biomass growth, all or a portion of the algal biomass is harvested from within the growth module 105. Examples of algal biomass growth techniques suitable for the growth module 105 are disclosed in US patent application publication nos. 2021/0260527; 2016/0194599; and 2014/0127776, all of which are incorporated herein in their entirety by reference.

Some embodiments of algal biomass growth techniques may utilize a substrate upon which algal biomass is grown (i.e., cultivated). The substrate may be a material that provides a physical structure upon which algal biomass growth occurs. The substrate may be functionalized with a layer of material that enables photosynthetic activity—i.e., carbon dioxide capture coating (i.e., a biomass cultivation media) that provides for growth of algal biomass. Such functionalized substrate may include a substrate that provides physical structure that has a layer of hydrogel formed thereon, where algae is admixed with the hydrogel or on one or more surfaces of the hydrogel. In some embodiments, algal biomass growth may occur directly on one or more surfaces of the functionalized substrate. Harvesting of the biomass may include removal of the functionalized substrate from within an interior space of the growth module 105 and, optionally, may include removal of all or part of the carbon dioxide capture coating (and algal biomass thereof) from the functionalized substrate by a suitable means (e.g., physical removal, removal with a stream of air, removal with a stream of water).

The drying module 110 (e.g., a second system module) serves to reduce the moisture content of carbon dioxide capture coating harvested from within the growth module 105. The harvested carbon dioxide capture coating may remain in combination with the substrate when placed within the drying module or may be removed from the substrate prior to placement within the drying module. Such drying may be carried out using a variety of different mechanisms and sources of energy. The harvested carbon dioxide capture coating, which includes grown algal biomass therein or thereon, may be subjected to an ambient or forced evaporative process. The harvested carbon dioxide capture coating, which includes grown algal biomass therein or thereon, may be subjected to a physical process for forcibly reducing hydration of the harvested biomass within or prior to being placed within the drying module 110—e.g., direct compression, centrifuging, tumbling, and the like).

The harvested carbon dioxide capture coating may be subjected to heating (ambient or powered) for thermally reducing hydration of the harvested biomass. In some embodiments, the drying module 110 may have a construction similar to the growth module for enabling sunlight to provide energy (e.g., via direct sunlight) for drying the harvested carbon dioxide capture coating. In some embodiments, thermal energy for drying the harvested carbon dioxide capture coating functionalized substrate may be provided via a powered heating device (e.g., powered via electricity, combustible oil, natural gas, or the like).

The drying module 110 may be constructed and operable to reduce moisture within the harvested carbon dioxide capture coating to below a specified threshold, reducing moisture within the harvested carbon dioxide capture coating by a specified amount (e.g., 80% from as-harvested moisture content), and the like. For example, the drying module 110 may include a moisture content monitoring device operable for monitoring a level of moisture therein and, optionally, the moisture content monitoring device may be coupled to a pump and/or the valve for enabling operation of the pump or valve as a function of the level of moisture content in the drying module 110 (e.g., including within a volume of the biomass). Substrate carrying harvested carbon dioxide capture coating may be hung vertically to allow for water evaporation, resulting in a desiccated algal biomass (e.g., including any cultivation media). Steps may be taken to prevent wrinkling of the substrate as it is dried such as, for example, implementing controlled or slow drying, flattening the substrate via mechanical means, or the like. Substrate carrying harvested carbon dioxide capture coating having been dried in the drying module 110 may have an additional layer of carbon dioxide capture coating formed over the dried layer and then deployed back into the growth module 105 for enabling growth of algal biomass within or on the additional layer of carbon dioxide capture coating. The underlying objective of the drying module 110 is to achieve dried carbon dioxide capture coating (and algal biomass thereof) having a moisture content that supports long-term sequestration of the dried carbon dioxide capture coating with only an acceptable level of re-emission of carbon dioxide therefrom.

The inventor has discovered that sufficient desiccation (i.e., drying) of a layer of harvested carbon dioxide capture coating provides for sequestration of at least a portion of algal biomass residing (e.g., grown) within the layer of harvested carbon dioxide capture coating. Particularly, a carbon dioxide capture coating in the form of a hydrogel has the characteristic of supporting not less than a minimum target growth rate of algal biomass therein when in a first state of hydration (e.g., at or above an upper limit threshold (e.g., not less than 50% of a maximum hydrated state)) and sequestering the algal biomass therein when in a second state of hydration (e.g., at or below a lower limit threshold (e.g., not greater than 10% of the maximum hydrated state)). In the first state of hydration, a layer of the carbon dioxide capture coating exhibits a physical matrix providing sufficient gas exchange between an interior volume of the carbon dioxide capture coating and a gaseous atmosphere surrounding the carbon dioxide capture coating. In the second state of hydration, in addition to possessing inadequate amounts of hydration for readily supporting photosynthesis, the physical matrix of the layer of the carbon dioxide capture coating constricts and/or becomes otherwise altered to thereby limit gas exchange required for supporting photosynthesis. In these regards, it is disclosed herein that systems and methods in accordance with embodiments of the disclosures made herein provide for "in-film" sequestration of algal biomass.

The sequestration module 115 (e.g., a third system module) serves to store dried carbon dioxide capture coating in a manner that inhibits or significantly limits re-emission of carbon dioxide from (i.e., sequesters) the dried carbon dioxide capture coating during storage. The sequestration module 115 is limited to being able to store dried carbon dioxide capture coating and algal biomass thereof up to only a maximum storage volume of the sequestration module 115. The sequestration module 115 has a sealable opening that readily allows for additional quantities of dried carbon dioxide capture coating to be added to an interior space of the sequestration module 115. Substrate, cultivation media, carbon dioxide capture coating with algal biomass, and combinations thereof may be shredded or otherwise converted to smaller format pieces to enhance volumetric density of contents of the sequestration module 115. To this end, the sequestration module 115 may provide an enclosed interior (e.g., sealed) space having a climate that inhibits or significantly limits chemical activity within the dried carbon dioxide capture coating that would otherwise result in unrestricted liberation of carbon dioxide from the dried carbon dioxide capture coating. Such climate may include one which has one or more of a controlled amount of humidity, a controlled maximum temperature, a controlled amount of light, a controlled amount of ambient pressure, or the like. The underlying objective of the sequestration module 115 is to store dried carbon dioxide capture coating and algal biomass thereof under conditions that maintain biological and chemical activity within the dried biomass within acceptable ranges.

The storage module 120 (e.g., a fourth system module) serves a similar purpose as the sequestration module 115. Specifically, like the sequestration module 115, the underlying objective of the storage module 120 is to store dried and algal biomass thereof (and algal biomass thereof) under conditions that maintain biological and chemical activity within the dried and algal biomass thereof within acceptable ranges. To this end, the storage module 120 may have a sealed interior space. A key difference between structure and functionality of the storage module 120 as compared to the sequestration module 115 is volume of dried and algal biomass thereof which the storage module 120 may store and the manner in which it is stored. For example, whereas the sequestration module 115 may be limited to storing up to only a maximum storage volume of the sequestration module 115, the storage module 120 may have an enclosed interior (e.g., sealed) space to store a plurality of the sequestration modules 115 therein (e.g., a 40 ft. HI-cube shipping container) or to itself serve as a sequestration module in place of or in addition to one or more of the sequestration modules 115 (e.g., no discrete modules within the storage modules 120).

In some embodiments, following sequestration and/or storage in accordance with embodiments of the disclosures made herein (e.g., for enabling sufficient amounts of biomass for post-processing), pyrolysis may be used for achieving durable sequestration of the dried biomass. Durable sequestration refers to biomass being maintained in a form and/or location that precludes its re-emission to the Earth's atmosphere for a climatically-significant duration of time—e.g., 100 years or more. It is well known that pyrolysis of biomass, such as for example algal biomass, produces combinations of biochar, bio-oil, and syn-gas. It is well known that the biochar may be deposited within an earthen storage location (e.g., buried in soil or a subterranean space) for achieving its durable sequestration and that the bio-oil and syn-gas are sustainable fuels that may be used for producing energy within or exterior to a system used to produce algal biomass (e.g., used to produce electricity and/or thermal energy within the system 100).

Figure 4:
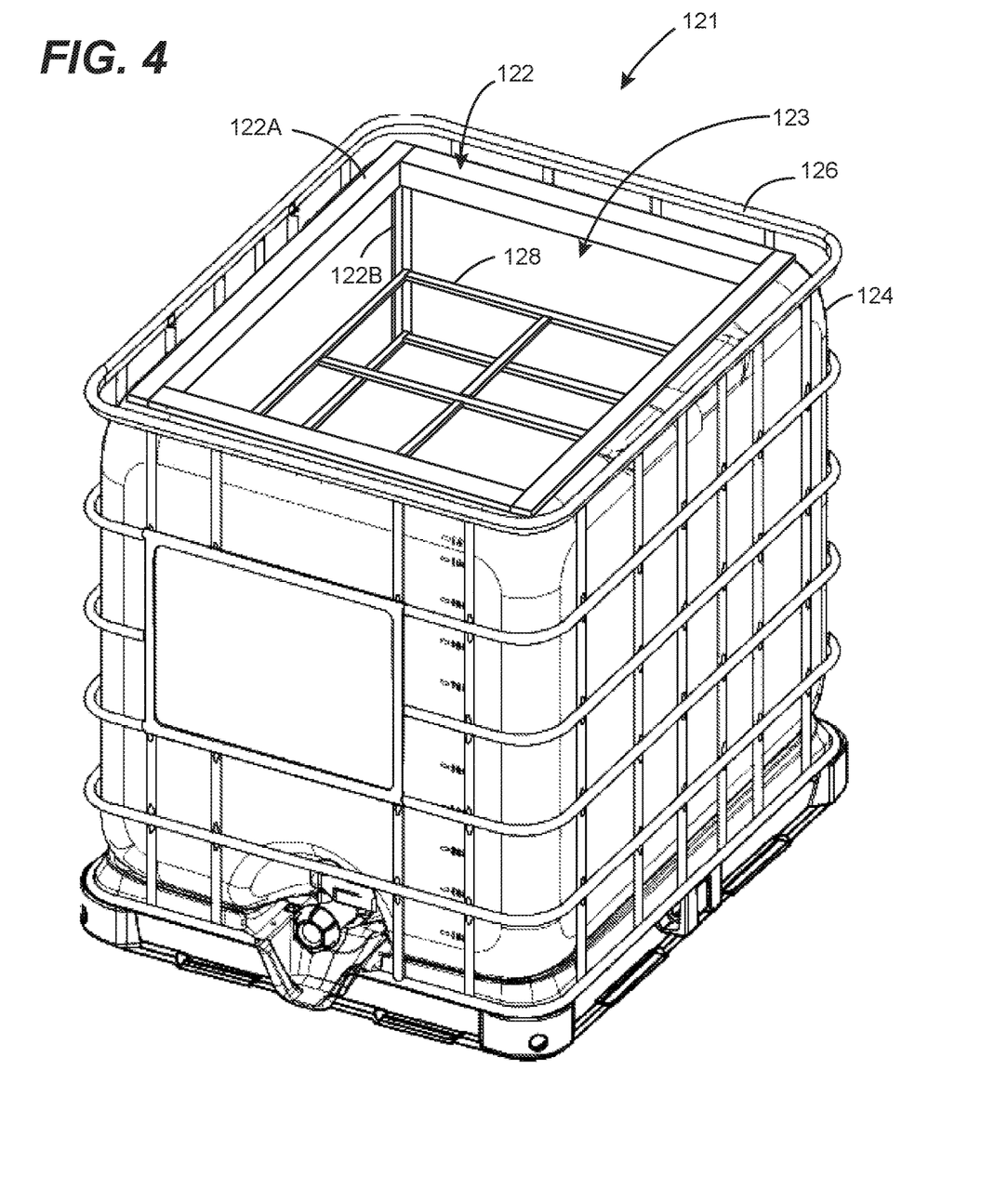
FIG. 4 is a perspective view showing an intermediate bulk container modified to function as a growth container of the system 100.

Turning now to structure and construction of the growth module 105, as shown in FIG. 4, the drying module 110, and the sequestration module 115, such modules may be constructed from Intermediate Bulk Cargo containers (IBCs), which are well known. In some embodiments, an IBC (i.e., a module enclosure) may be modified to mechanically accept one or more carbon dioxide capture devices therein. For example, an IBC 121 may be adapted to accept a substrate support 122 within an opening formed (e.g., cut) within a surface (e.g., top surface) of a fluid containment body 124 of the IBC 121 to provide for access to an internal space 123 of the fluid containment body 124. The fluid containment body 124 is a container in which the one or more one or more carbon dioxide capture devices are located and the fluid containment body 124 is retained within a structural frame 126 of the IBC 121. As is well know, the structural frame 126 enables stacking of a plurality of IBCs 121 and provides physical protection of the fluid containment body 124.

Figure 5:
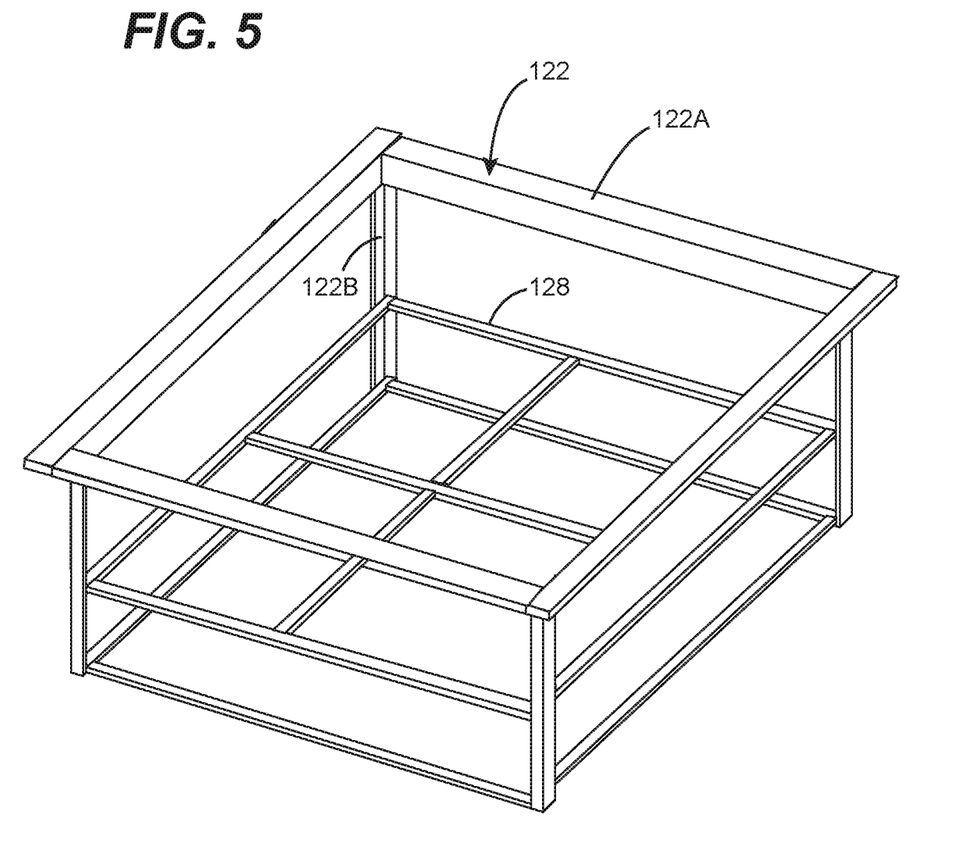
FIG. 5 is a perspective view showing a substrate support body of the intermediate bulk container of FIG. 4.

The substrate support 122 is constructed and dimensioned to fit into the opening formed in the surface of the fluid containment body 124. A mounting portion 122A (FIG. 5) of the substrate support 122 is engaged with a top surface of the fluid containment body 124. A substrate support portion 122B of the substrate support 122 is attached to the mounting portion 122A and is positioned within the fluid containment body 124 below the opening therein. One or more functionalized substrate may be engaged directly with the substrate support portion 122B of the substrate support 122 or may be engaged with the substrate support portion 122B of the substrate support 122 via a substrate support tray 128 engaged with the substrate support 122B. The substrate support 122 and/or the substrate support tray 128 may be configured to support substrate in a horizontal, vertical, or other orientation. The substrate support body and/or the substrate support tray 128 may be configured for enabling adjustment of vertical placement of the functionalized substrate such as to, for example, alter intensity of the light to which the functionalized substrate is exposed.

Figure 6:
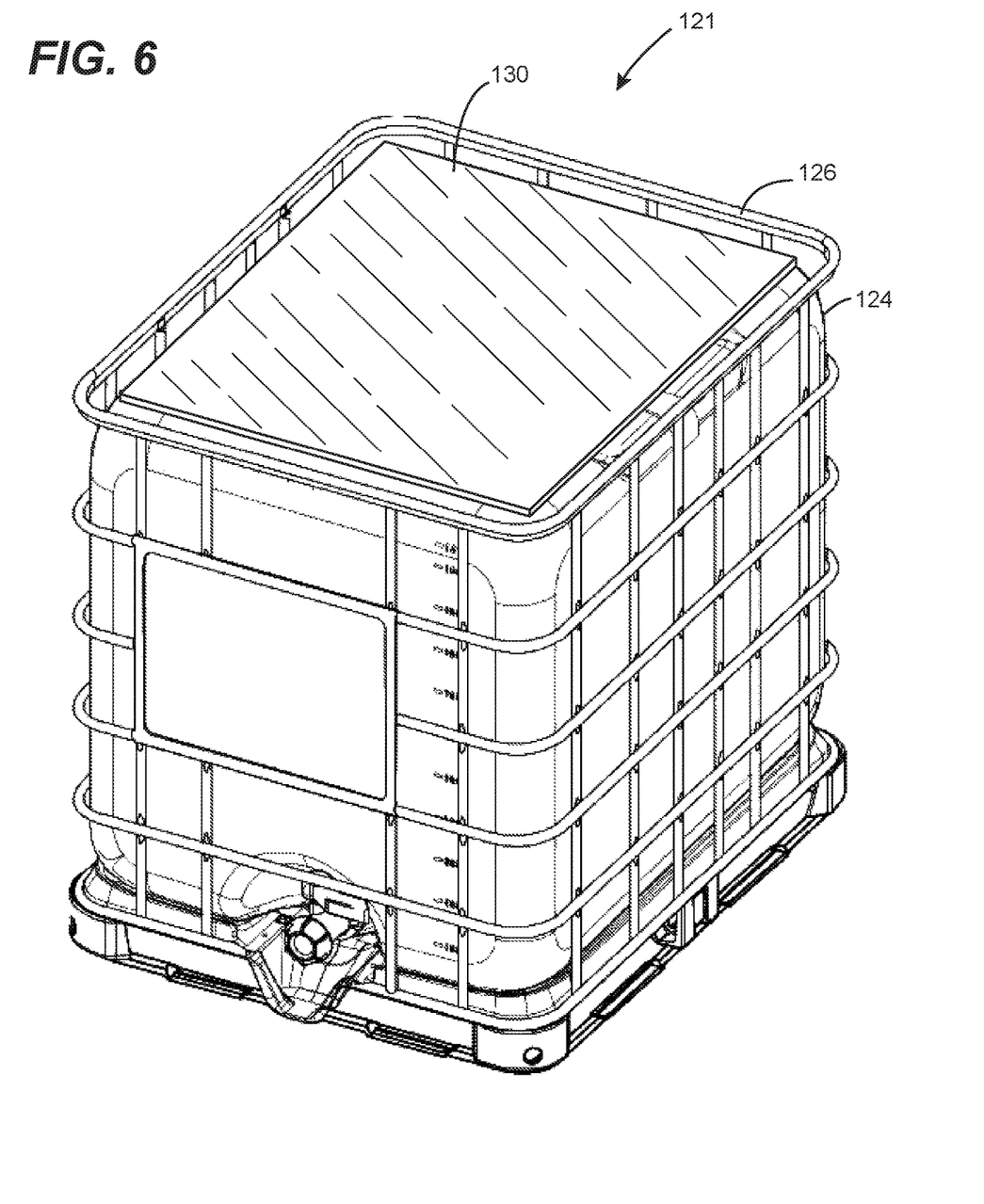
FIG. 6 is a perspective view showing the intermediate bulk container of FIG. 4 with a top cover in place.

For a growth module 105 that may have a sealed interior space, as shown in FIG. 6, a top cover 130 may be used as a body with which a seal is created for sealing closed the interior space 123 (e.g., a seal member positioned between the fluid containment body 124 and the top cover 130). For example, the top cover 130 may have sufficient weight to compress a sealing body between the top cover 130 and the fluid containment body 124 (i.e., a main body) of the growth module 105. Alternatively, for example, a fastening arrangement may be used for securing the top cover 130 to the fluid containment body 124.

The growth module 105 may have a construction that permits a specified amount and/or type of light to pass into an interior space 123 of the fluid containment body 124. In some embodiments, such light control may be provided for via the top cover 130 made of, for example, glass or polymeric (e.g., acrylic or polycarbonate) material (light transmission body) that is transparent or translucent and that may be configured to provide light filtering and/or rejection. For example, the top cover 130 may be a transparent or translucent layer of material and may have a light filtering fabric (e.g., plant shade fabric) or solar tint film attached or otherwise engaged therewith. The drying module may include a light transmissive top cover having a layer of solar control film thereon or material dispersed therein that provides for light transmission control—e.g., rejects UV rays and/or other portions of sunlight impinging thereon (e.g., up to at least 50%, 70%, or 90% rejection of the UV rays of sunlight impinging thereon).

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A carbon dioxide capture and sequestration system, comprising:
    a growth module comprising a first interior enclosed space within which algal biomass is grown;
    a drying module comprising a second interior enclosed space within which at least a portion of algal biomass harvested from within the growth module is dried;
    a sequestration module comprising a third interior enclosed space within which at least a portion of the dried algal biomass is stored; and
    a carbon dioxide recapture apparatus, wherein the carbon dioxide recapture apparatus includes at least one conduit coupled to the first interior enclosed space of the growth module, the second interior enclosed space of the drying module, and the third interior enclosed space of the sequestration module for routing to the growth module carbon dioxide off-gassed from at least one of the harvested algal biomass within the drying module and the dried algal biomass within the sequestration module.

2. The carbon dioxide capture and sequestration system of claim 1 wherein at least one of a pump and a valve is operably connected to at least one of the conduits, the growth module, the drying module, and the sequestration module to cause the routing of the carbon dioxide to the growth module.

3. The carbon dioxide capture and sequestration system of claim 1 wherein a monitoring device is mounted within at least one of the drying module and the sequestration module for enabling a respective level of carbon dioxide therein to be monitored.

4. The carbon dioxide capture and sequestration system of claim 3 wherein at least one of a pump and a valve is operably connected to at least one of the conduits, the growth module, the drying module, and the sequestration module.

5. The carbon dioxide capture and sequestration system of claim 4 wherein:
    the at least one of the pump and the valve is coupled to the monitoring device; and
    the at least one of the pump and the valve is adapted to operate as a function of the respective level of carbon dioxide within the associated one of the associated conduits, the growth module, the drying module, and the sequestration module.

6. The carbon dioxide capture and sequestration system of claim 1 wherein
- at least one of a pump and a valve is operably connected to at least one of the drying module and one of the conduits attached to the drying module; and
- the drying module includes a moisture content monitoring device operable for monitoring a level of moisture therein; and
- the moisture content monitoring device is operably coupled to the at least one of the pump and the valve for enabling operation of the at least one of the pump and the valve as a function of the level of moisture content in the drying module.

7. The carbon dioxide capture and sequestration system of claim 1 wherein the drying module include a light transmissive top cover that rejects at least 70% of UV rays of sunlight impinging thereon.

8. The carbon dioxide capture and sequestration system of claim 7 wherein at least one of a pump and a valve is operably connected to at least one of the at least one conduit, the growth module, the drying module, and the sequestration module.

9. The carbon dioxide capture and sequestration system of claim 7 wherein a monitoring device is mounted within at least one of the drying module and the sequestration module for enabling a respective level of carbon dioxide therein to be monitored.

10. The carbon dioxide capture and sequestration system of claim 9 wherein at least one of a pump and a valve is operably connected to at least one of the at least one conduit, the growth module, the drying module, and the sequestration module.

11. The carbon dioxide capture and sequestration system of claim 10 wherein:
- the at least one of the pump and the valve is coupled to the monitoring device; and
- the at least one of the pump and the valve is adapted to operate as a function of the respective level of carbon dioxide within an associated one of the at least one conduit, the growth module, the drying module, and the sequestration module.

12. The carbon dioxide capture and sequestration system of claim 7 wherein
- at least one of a pump and a valve is operably connected to at least one of the drying module and a conduit attached to the drying module; and
- the drying module includes a moisture content monitoring device operable for monitoring a level of moisture therein; and
- the moisture content monitoring device is operably coupled to the at least one of the pump and the valve for enabling operation of the at least one of the pump and the valve as a function of the level of moisture content in the drying module.

13. The carbon dioxide capture and sequestration system of claim 1 wherein:
- the drying module includes a housing comprising a fluid containment body, a structural frame, a substrate support body, and a light transmissive top cover;
- the fluid containment body has an opening within a top surface thereof;
- the substrate support body includes a substrate support portion within the fluid containment body and below the opening therein; and
- the light transmissive top cover extends over the opening.

14. The carbon dioxide capture and sequestration system of claim 13 wherein:
- the substrate support portion is a first portion of the substrate support body; and
- the substrate support body includes a second portion engaged with a top surface of the fluid containment body.

15. The carbon dioxide capture and sequestration system of claim 13 wherein the light transmissive top cover rejects at least 70% of UV rays of sunlight impinging.

16. The carbon dioxide capture and sequestration system of claim 15 wherein:
- the substrate support portion is a first portion of the substrate support body; and
- the substrate support body includes a second portion engaged with a top surface of the fluid containment body.

17. The carbon dioxide capture and sequestration system of claim 13 wherein at least one of a pump and a valve is operably connected to at least one of the at least one conduit, the growth module, the drying module, and the sequestration module.

18. The carbon dioxide capture and sequestration system of claim 17 wherein:
- the substrate support portion is a first portion of the substrate support body; and
- the substrate support body includes a second portion engaged with a top surface of the fluid containment body.

19. The carbon dioxide capture and sequestration system of claim 17 wherein the light transmissive top cover rejects at least 70% of UV rays of sunlight impinging.

20. The carbon dioxide capture and sequestration system of claim 19 wherein:
- the substrate support portion is a first portion of the substrate support body; and
- the substrate support body includes a second portion engaged with a top surface of the fluid containment body.

* * * * *